(12) United States Patent
Hopkins et al.

(10) Patent No.: US 6,537,237 B1
(45) Date of Patent: Mar. 25, 2003

(54) ORTHOTIC DEVICE

(75) Inventors: Ronald B. Hopkins, Virginia Beach, VA (US); Richard T. Sieller, Virginia Beach, VA (US)

(73) Assignee: R & R Holdings, LLC, Virginia Beach, VA (US)

( * ) Notice: Subject to any disclaimer, the term of this patent is extended or adjusted under 35 U.S.C. 154(b) by 0 days.

(21) Appl. No.: 09/964,636

(22) Filed: Sep. 28, 2001

(51) Int. Cl.$^7$ .................................................. A61F 5/00
(52) U.S. Cl. .............................. 602/5; 602/16; 602/20; 602/23
(58) Field of Search .................. 602/16, 20, 23–27, 602/5; 601/33, 34; 482/112, 118

(56) References Cited

U.S. PATENT DOCUMENTS

| | | |
|---|---|---|
| 4,100,918 A | 7/1978 | Glancy |
| 4,191,373 A | 3/1980 | Lancellotti |
| 4,408,600 A | 10/1983 | Davis |
| 4,682,776 A * | 7/1987 | Mitchell et al. ............ 403/111 |
| 4,763,901 A | 8/1988 | Richter |
| 4,805,606 A | 2/1989 | McDavid, III |
| 4,838,251 A | 6/1989 | Chignon et al. |
| 4,862,878 A | 9/1989 | Davison et al. |
| 5,020,525 A * | 6/1991 | Ewing et al. ................ 602/27 |
| 5,117,814 A | 6/1992 | Luttrell et al. |
| 5,167,612 A | 12/1992 | Bonutti |
| 5,213,094 A | 5/1993 | Bonutti |
| 5,337,737 A | 8/1994 | Rubin et al. |
| 5,352,190 A | 10/1994 | Fischer et al. |
| 5,365,947 A | 11/1994 | Bonutti |
| 5,383,845 A | 1/1995 | Nebolon |
| 5,437,611 A | 8/1995 | Stern |
| 5,503,619 A | 4/1996 | Bonutti |
| 5,611,764 A | 3/1997 | Bonutti et al. |
| 5,683,336 A | 11/1997 | Pape |
| 5,685,830 A | 11/1997 | Bonutti |
| 5,857,988 A * | 1/1999 | Shirley ....................... 435/375 |
| 5,865,714 A | 2/1999 | Marlowe |
| 5,891,079 A | 4/1999 | Barnes |
| 6,063,048 A | 5/2000 | Bodenschatz et al. |
| 6,113,562 A | 9/2000 | Bonutti et al. |
| 6,117,097 A | 9/2000 | Ruiz |

* cited by examiner

Primary Examiner—Danton D. DeMille
Assistant Examiner—Quang D. Thanh
(74) Attorney, Agent, or Firm—John H. Thomas, P.C.

(57) ABSTRACT

An orthotic device has first and second, elongated support members. The support members are pivotally connected at their respective proximal ends. The device further includes a tensioning member and a tensioning member retainer at the distal end of the first member. There are also first and second pairs of guides, each pair adapted to receive the tensioning member. Whereby the device may facilitate movement of a limb into either a flexed or extended position by placing the tensioning member in the first or second pair of guides respectively.

18 Claims, 4 Drawing Sheets

ORTHOTIC DEVICE

The present invention relates to an orthotic device able to apply dynamic or static forces to a joint in need of therapy. The combination of components acts to provide multiple functions through the variable positioning of selected components. The force generated by the components and their direction can be quantified and used in therapeutic treatment to provide treatment guidelines.

BACKGROUND OF THE INVENTION

There are many known orthotic devices including those specifically directed to rehabilitation of various joints such as elbows, knees, wrists and ankles. Typically, these apparatuses are static or have a single pressure/force that is applied during operation. Those forces may be uneven across the device. Usually, the forces are focused solely on extension or flexion, but not both.

One problem with conventional devices is the inability to easily customize those devices for a particular patient. A given arrangement may be useful and appropriate for one patient, but not as effective for another. Further, those devices may be difficult to adjust between, for instance, flexion or extension. Also, typical devices are not able to easily vary their tension and quantify such for a given patient. For instance, a weak or frail patient may require less tension or force during therapy than a large or strong patient. Also, as a patient gains strength during therapy, the device needs to be able to be variable as the therapy process moves forward.

SUMMARY OF THE INVENTION

Accordingly, it is an object of the present invention to overcome the forgoing drawbacks and problems. The present invention provides a combination of components that provide multiple functions and can be arranged to produce varied directional forces. The forces generated by the present device can be quantified and used in therapeutic treatment to provide treatment guidelines.

In one embodiment, the orthotic device comprises first and second limb support members which are pivotally connected at their respective proximal ends. The orthotic device further includes tensioning means and a first center post positioned at the distal end and at substantially the middle of the first member. There is also a second center post adapted to receive the tensioning member and positioned at the distal end and at substantially the middle of the second member. First and second pairs of guides are adapted to receive the tensioning member. The first pair of guides is positioned at the distal end of the first member and at opposite sides of the first member. The second pair of guides is positioned at the proximal end of the second member and at substantially the middle of the member. The first and second pairs of guides are positioned so that when the tensioning member is placed in the first guides and around the second center post, a flexion moment is created; and when the tensioning member is placed around both the first and second center posts and in the second guides, an extension moment is created. Accordingly, when the device is fitted to a patient's limb connected by a joint, the limb can be urged to either a flexed or extended position by placing the tensioning member in the first or second guides respectively. The tensioning member may further comprise means for varying the length of the tensioning member. The second center post may comprise a pulley. The pulley may further comprise a tension gauge that measures and displays the amount of tension exerted by the tensioning member. The tensioning member can be a single, noncontinuous piece that is releaseably secured at each end to the first center post. The pivotable connection between the support members may comprise a range of pivot limiter.

In a further embodiment, an orthotic device comprises first and second elongated support members, wherein the support members are pivotally connected at their respective proximal ends. The device further includes a tensioning member and first and second post means for retaining the tensioning member at the distal ends of the first and second members respectively. There are also first and second pairs of means for guiding the tensioning member. The first pair of guide means is positioned at the distal end of the first member and on opposite sides of the member. The second pair of guide means is positioned at the proximal end of the second member and at substantially the middle of that member. When the tensioning member is placed in the first pair of guide means and around the second post means, a flexion moment is created; and when the tensioning member is placed around both the first and second post means and in the second pair of guide means, an extension moment is created. Therefore, when the device is fitted to a patient's limb connected by a joint, the limb can be urged to either a flexed or extended position by placing the tensioning member in the first or second guide means respectively. The tensioning member may further comprise means for varying the length of the tensioning member. The second post means may comprise means for equalizing tension along the tensioning member. The tension equalizing means may further comprise a tension gauge that measure and displays the amount of tension exerted by the tensioning member. The tensioning member can be a single, noncontinuous piece that is releasably secured at each end to the first post means. The second post means may comprise a means for equalizing tension along the tensioning member. The pivotal connection between the support members may comprise a range of pivot limiter.

In a still further embodiment, an orthotic device comprises first and second elongated support members, wherein the support members are pivotally connected at their respective proximal ends. The device further comprises a tensioning member and a plurality of guides adapted to receive the tensioning member wherein the guides allow a user to change the directional force created by the tensioning member on the support members.

DETAILED DESCRIPTION OF THE PREFERRED EMBODIMENTS

Figure 1:
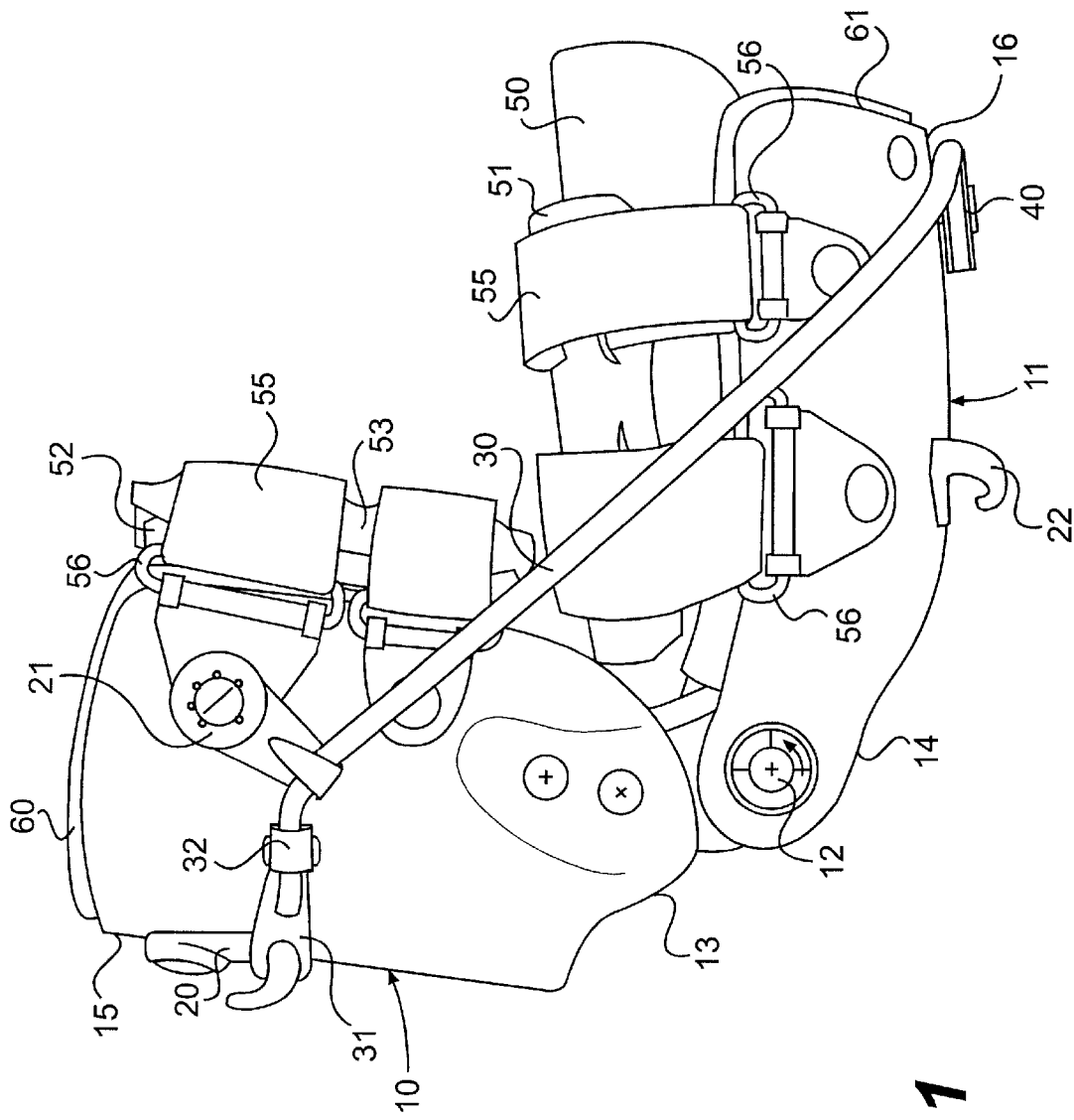
FIG. 1 is a side elevation view of one embodiment of a device in accordance with the present invention with the device shown in a flexed position.

The present invention is intended for use with a joint such as an elbow, knee, wrist or ankle. The specific embodiment shown in FIGS. 1 through 4 describes an elbow brace. Of course, the teachings may be applied to other devices for other joints in accordance with the present teachings.

The elbow brace shown in FIGS. 1 through 4 includes a first limb support member 10 and a second limb support member 11. These particular support members are elongated cuffs made primarily of a stiff plastic material. The support members 10 and 11 will typically come in different sizes to fit different sized arms. It is also possible that an orthotic device may be custom molded to accurately fit a specific arm of a given patient.

The first member 10 is adapted to support an upper arm. The first member 10 has a proximal end 13 adjacent the second member 11 and a distal end 15 on the opposite end of the elongated first member 10. The second member 11 is adapted to support a forearm. It is made up of a proximal end 14 adjacent the first member 10 and a distal end 16. Both the first and second members 10 and 11 are roughly in the shape of a half tube adapted to wrap a substantial way around a patient's limb to support it. The proximal ends 13 and 14 are connected by a hinge 12 in order to allow the device to flex and extend with the limb being braced. The hinge 12 defines the mechanical axis of rotation of the brace. The anatomical axis of the limb (in this example an elbow) will be approximately the same as the mechanical axis of the brace.

A person's limb, in this case an arm, is held within the device by straps 55 that connect the opposite sides of the respective first and second members 10 and 11. The straps 55 extend from one side of the members 10 and 11 across through a loop 56 and back onto themselves. The straps 55 are preferably made from conventional hooks and loops (Velcro) to secure the person's limb within the device. Soft plastic sleeves 50 and 52 are positioned inside the straps 55 through use of pads 51 and 53 in order to better secure the patient's limb and to make the device more comfortable overall. Additionally, pads 60 and 61 may line the insides of the first and second members 10 and 11 to add in the comfort and fit of the brace.

The device as described thus far is conventional. The sleeve elements and the straps and a hinge assembly are all used with various alternatives in the construction of limb braces/orthotic devices generally. The following teachings with respect to the positioning and variability of a tensioning means may be applied to any of these conventional type braces whether or not the underlying components are exactly as described herein thus far.

A tensioning means 30 can be any type of elastic member including a rubber cord, plastic or metal spring, or any other type of elastic member. As shown in the drawings, the tensioning means 30 is a rubber cord or bungee cord. The tensioning means 30 is a single noncontinuous piece, but it could alternatively be a continuous loop. Also, more than one elastic member can make up a tensioning means. The tensioning means 30 has ends 31 that are attached to a tensioning member through clamps 32. Alternatively, instead of a permanent clamp 32, there may be an adjustable piece 35 that allows the tensioning means 30 to be lengthened or shortened. This length adjuster piece 35 can be simply two slots or can be any other type of adjustable clamping mechanism. The ends 31 further have holes that are adapted to hook over to latch onto two retaining hooks 20. The retainer hooks 20 may be one or, as shown, a pair of hooks. They may be any other type of post or other anchoring device to engage and hold the ends 31 of the tensioning member 30. The retainer hooks 20 or other type of post should be positioned on the outer surface of and in approximately the center or middle of the distal end 15 of the first member 10.

Figure 4:
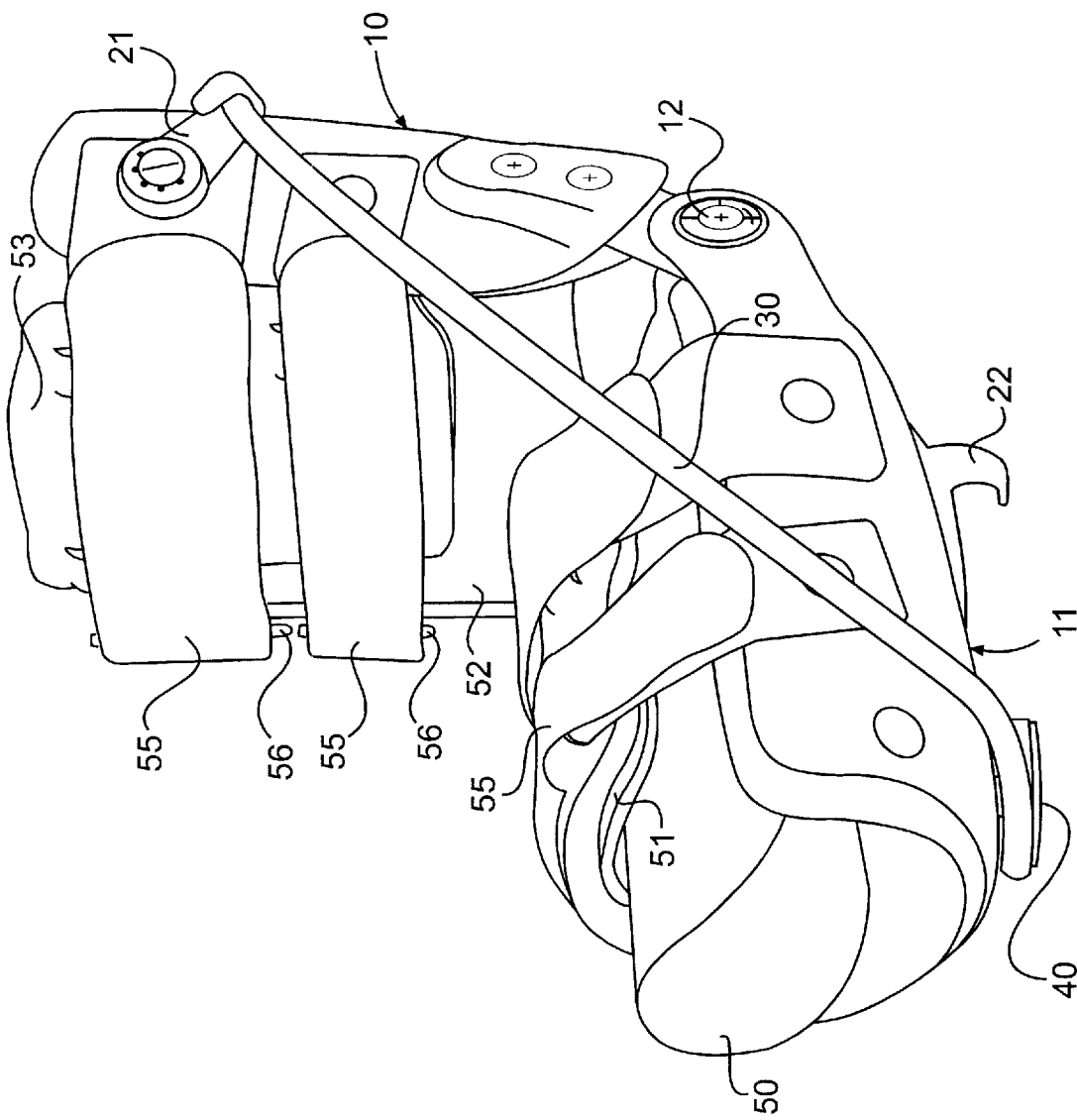
FIG. 4 is a perspective view of one embodiment of a device in accordance with the present invention with the device shown in a flexed position.

When in the flexed positioned as shown in FIGS. 1 and 4, the tensioning means 30 loops through the pair of guides 21 and around pulley 40. When the tensioning member is the appropriate length, it will create a steady and constant force urging the arm within the device into the flexed position. By varying the length of the tensioning means 30, the amount of tension urging the device/patient's limb into the flexed position may be varied. The guides 21 are simply hooks like hooks 20. The retainer hooks 20 are positioned on the outer surface and at the distal end of the first member 10 in approximately the center or middle of the member. The guides 21 are positioned at the distal end of the first member, but on opposite sides of the retainer hooks 20. The pulley 40 is positioned at the distal end 16 of the second member 11 and substantially at the middle of the second member.

Figure 2:
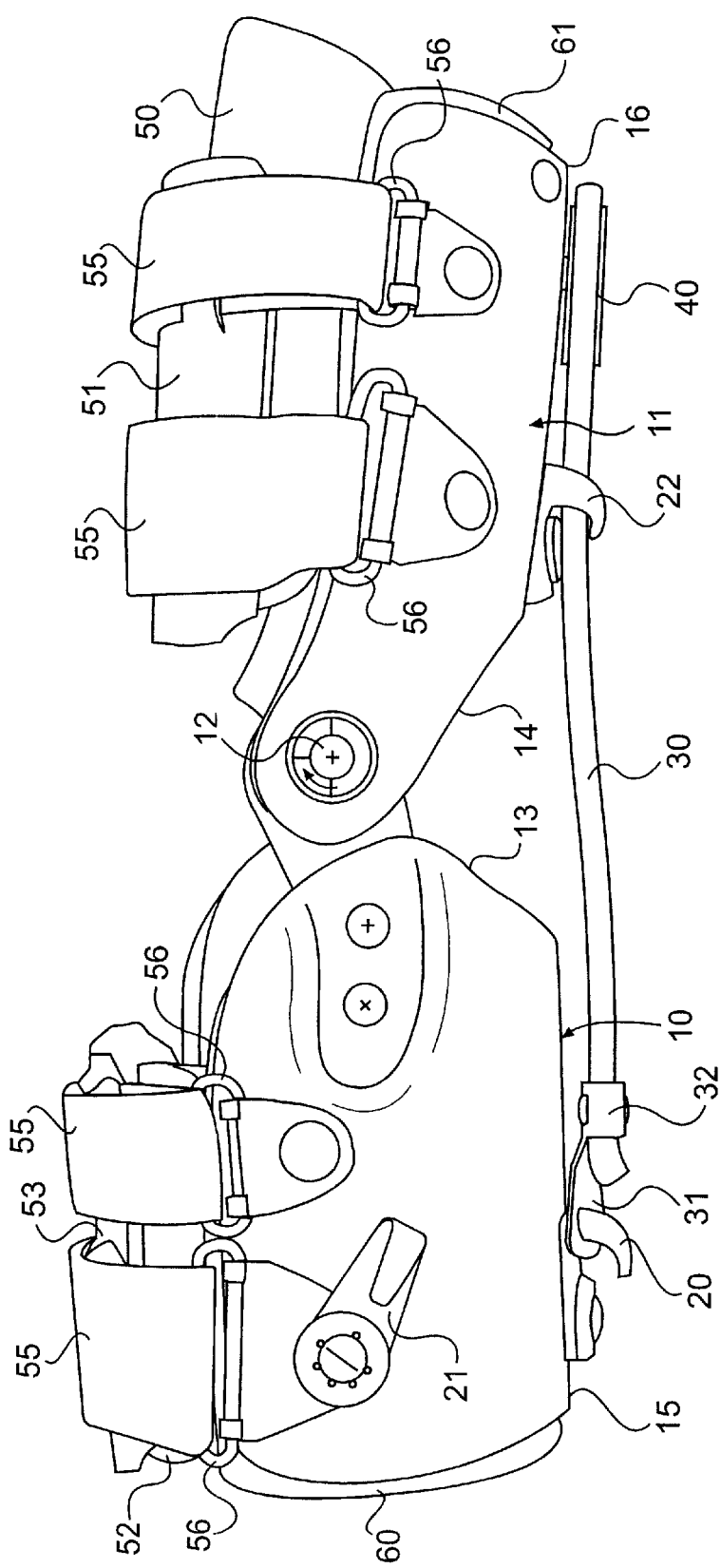
FIG. 2 is a side elevation view of one embodiment of a device in accordance with the present invention with the device shown in an extended position.
Figure 3:
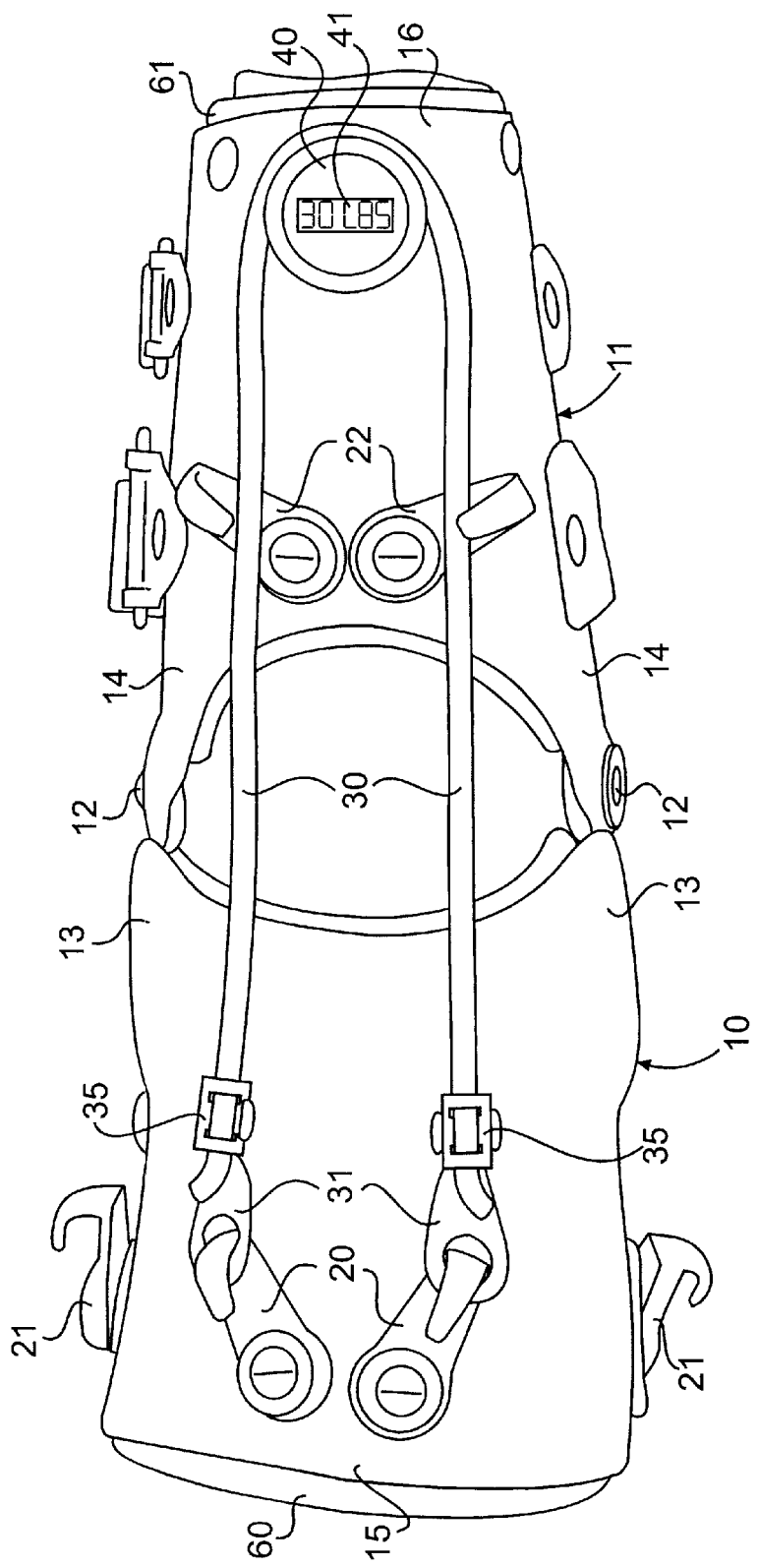
FIG. 3 is a top elevation view of one embodiment of a device in accordance with the present invention with the device shown in an extended position.

In the extended position as shown in FIGS. 2 and 3, the tensioning means 30 is attached to the retainer hooks 20 and looped around the pulley 40. The tensioning means 30 is further placed within the guides 22. The guides 22 are positioned on the outer surface and in the middle of the proximal end 14 of the second member 11. In this way, the device is pulled to the extended position.

As illustrated in the alternative figures, the brace may be urged to the extended or flexed position by placement of the tensioning means 30 within guides 21 (flexed position) or guides 22 (extended position). For ease of use, the guides 21 and 22, as well as the retainers 20 are hooks. Other types of retainers or guides may be used to receive and hold the tensioning means 30 so that it is urging the brace in the flexed or extended positions. Also, as noted earlier, the tensioning means 30 may be a continuous loop. Placement of the tensioning means 30 as described above is equally applicable to a continuous loop. The primary difference is that a center post (either one or more) rather than retainer hooks 20 can be used to hold a tensioning member about the center (middle) of the distal end of the second member. Similarly, if the tensioning means 30 is a plurality of elastic members, then the device designer will use the teachings herein to position a sufficient number of posts and/or hooks to achieve the same or similar results obtained herein.

The precise placement of the guides 21 or 22 will be a matter of choice by a given therapist. As shown, the guides 21 and 22 (as well as the center post 20) are hooks that are attached by screws to the first and second limb members 10 and 11. Generically speaking, guides or posts may be mounted in slots that allow a therapist to move the guides or post on the members. There may also be predrilled holes to receive the screws that anchor the guides or posts in the member. In operation, it is only essential that the guides 21 in conjunction with the pulley 40 (or any center post at the distal end of the second member 11) create a force that causes a flexion moment. That is, the force of a tensioning member must be on the correct side of the anatomical/mechanical axis to draw the ends of the members towards each other in a flexion or extension rotation. Accordingly, the guides 21 that position the tensioning member 30 so that it causes a flexion moment are oriented on the side of the anatomical and mechanical axes to create that flexion moment. The alternative to the flexion moment is the creation of an extension moment where the tensioning member 30 is oriented along the center of the members 10 and 11 and on the outside of the anatomical/mechanical axis of the brace when worn by a user. (For the purposes of this relative discussion, from a side view, the "outside" is the side having the members 10 and 11, and the "inside" is the side having the straps 55). The guides 22 are relatively centered as are the retaining hooks 20 (or any center post) and pulley (any center post). As shown in FIG. 2, therefore, the tensioning means is on the outside of the anatomical/mechanical axis and therefore creates an extension moment. In order to create a flexion moment force, guides such as guides 21 will be positioned on the opposite and relatively inside of a brace, while the extension guides such as guides 22 will be oriented along the center or outside of a brace.

The pulley 40 is a tension equalizing device in that it equalizes the forces of the tensioning member 30 on each side of the device. This allows for balanced and equal forces in therapy. While a pulley 40 is envisioned as preferable, any post centered at the distal end 16 of the second member 11 can work. For instance, a smooth or low friction post in combination with a low friction surface on a cord could also allow equalization of the tension along the cord. Also, as best seen in FIG. 3, the pulley 40 can have engineered into it a tension gauge 41 that measures and displays the amount of tension being exerted by the tensioning member 30. The tension gauge 41 may be used in conjunction with the length adjustor piece 35 in order to accurately apply a given tension pressure to a joint when the device is used in therapy. In other words, a therapist may want a very slight tension on a very painful joint. On the other hand, it may be desirable to exert a substantial tension in order to help straighten or bend a joint. By quantifying the amount of tension, a therapist is able to better monitor and control the specific therapy that is preferably administered for a given patient. These tension gauges are referred to as economy force gauges commercially available from McMaster-Carr, Inc.

Another alternative feature of the present invention includes the use of a range of pivot limiter in the hinge 12. By limiting the range of the pivot through known limiting devices, the patient's joint can be protected from abnormal force, preventing extreme range of motion and protecting from injury or damage to surgically placed registration. The use of this range of motion or range of pivot limiter with the hinge 12 is a still further therapy device that, particularly when combined with the tensioning member and guides discussed earlier, allows a therapist to deliver exactly a quantifiable and repeatable therapy to a joint. A therapist can prescribe and limit a specific range of motion and/or amount of tension, thereby removing the guess work from the therapy.

The example discussed in connection with the figures displays the pulley 40 on the relatively lower limb member 11 and the retaining hooks 20 on the relatively upper limb member 10. The placement of these components can be reversed with the other posts and guides being moved to similar opposite locations on the respective limb members.

A still further variation of the present invention is an orthotic device kit. This kit would include all of the parts described herein. Specifically, there would be first and second limb support members pivotally connectable at their respective proximal ends. There are first and second central tension receiving means. The first member would be adapted for affixing thereto, at substantially at the middle of its distal end, the first central tension receiving means. The second member is adapted for affixing thereto, at substantially at the middle of its distal end, the second central tensioning receiving means. The kit would further include first and second pairs of guides, each pair adapted to guide the tensioning means. The first member adapted for affixing thereto the first pair of guides at opposite sides of its distal end. The second member adapted for affixing thereto the second pair of guides at substantially the middle of its proximal end, wherein with the tensioning means positioned in the affixed first guides and received in the affixed second central means, a flexion moment is created; and with the tensioning means positioned in both the first and second affixed central means and in the fixed second guides, an extension moment is created. In summary, therefore, the kit is merely the separate list of components like those shown in FIGS. 1–4 but before their assembly.

While the invention has been described with reference to specific embodiments thereof, it will understood that numerous variations, modifications and additional embodiments are possible, and accordingly, all such variations, modifications, and embodiments are to be regarded as being within the spirit and scope of the invention.

What is claimed is:

1. An orthotic device comprising:
   first and second elongated support members, wherein the support members are pivotally connected at their respective proximal ends;
   a tensioning member;
   a first center anchoring device adapted to receive the tensioning member and positioned substantially at the middle of the distal end of the first member;
   first and second pairs of guides, each pair adapted to receive the tensioning member,
   the first pair of guides positioned at the distal end of the first member and at opposite sides of the first member,
   the second pair of guides positioned at substantially the middle of the proximal end of the second member;
   a second center anchoring device adapted to receive the tensioning member and positioned at substantially the middle of the distal end of the second member;
   wherein, when the tensioning member is placed in the first pair of guides and around the second center anchoring device, a flexion moment is created; and when the tensioning member is placed around both the first and second center anchoring devices and in the second pair of guides, an extension moment is created;
   whereby, when the device is adapted to fit to a patient's limb connected by a joint, the limb can be urged either a flexed or extended position by placing the tensioning member in the first or second guides respectively.

2. An orthotic device as described in claim 1, wherein the tensioning member further comprises means for varying the length of the tensioning member.

3. An orthotic device as described in claim 1, wherein the second center anchoring device comprises a pulley.

4. An orthotic device as described in claim 3, wherein the pulley further comprises a tension gauge that measures and displays the amount of tension exerted by the tensioning member.

5. An orthotic device as described in claim 1, wherein the tensioning member is a single, noncontinuous piece that is releasably secured at each end to the first center anchoring device.

6. An orthotic device as described in claim 5, wherein the second center anchoring device comprises a pulley.

7. An orthotic device as described in claim 3, wherein the pulley further comprises a tension gauge that measures and displays the amount of tension exerted by the tensioning member.

8. An orthotic device as described in claim 1, wherein the pivotal connection between the support members comprises a range of pivot limiter.

9. An orthotic device as described in claim 1, wherein the tensioning member is an elastic cord.

10. An orthotic device comprising:

first and second elongated support members, wherein the support members are pivotally connected at their respective proximal ends;

a tensioning member;

first and second anchoring device means for retaining the tensioning member at the distal ends of the first and second members respectively;

first and second pairs of means for guiding the tensioning member, the first pair of guide means positioned at the distal end of the first member and at opposite sides of the first member, the second pair of guide means positioned at the proximal end of the second member and at substantially the middle of the second member; and wherein, when the tensioning member is placed in the first pair of guide means and around the second anchoring device means, a flexion moment is created; and when the tensioning member is placed around both the first and second anchoring device means and in the second pair of guide means, an extension moment is created;

whereby, when the device is adapted to fit to a patient's limb connected by a joint, the limb can be urged to either a flexed or extended position by placing the tensioning member in the first or second pair of guide means respectively.

11. An orthotic device as described in claim 10, wherein the tensioning member further comprises means for varying the length of the tensioning member.

12. An orthotic device as described in claim 10, wherein the second anchoring device means comprises a means for equalizing tension along the tensioning member.

13. An orthotic device as described in claim 12, wherein the tension equalizing means further comprises a tension gauge that measures and displays the amount of tension exerted by the tensioning member.

14. An orthotic device as described in claim 10, wherein the tensioning member is a single, noncontinuous piece that is releasably secured at each end to the first anchoring device means.

15. An orthotic device as described in claim 14, wherein the second anchoring device means comprise a means for equalizing tension along the tensioning member.

16. An orthotic device as described in claim 12, wherein the tension equalizing means further comprises a tension gauge that measures and displays the amount of tension exerted by the tensioning member.

17. An orthotic device as described in claim 10, wherein the pivotal connection between the support members comprises a range of pivot limiter.

18. An orthotic device kit comprising:

first and second limb support members pivotally connected at their respective proximal ends;

tensioning means;

first and second central tension receiving means;

said first member adapted for affixing thereto, substantially at the middle of its distal region, said first central tension receiving means;

said second member adapted for affixing thereto, substantially at the middle of its distal region, said second central tensioning receiving means;

first and second pair of guides, each pair adapted to guide the tensioning means;

said first member adapted for affixing thereto said first pair of guides at opposite sides of its distal region;

said second member adapted to affix thereto said second pair of guides at substantially the middle of its proximal region;

wherein, with the tensioning means positioned in the affixed first pair of guides and received in the affixed second central tensioning receiving means, a flexion movement is created; and with the tensioning means positioned in both the first and second affixed central tensioning receiving means in the affixed second pair of guides, an extension movement is created;

whereby, when the device is adapted to fit to a patient's limb connected by a joint, the limb can be urged either in a flexed or extended position by placing the tensioning means in the first and second pair of guides respectively.

* * * * *